(12) United States Patent
Rouse et al.

(10) Patent No.: US 10,363,157 B2
(45) Date of Patent: Jul. 30, 2019

(54) TORQUE GENERATING POUCH AND RELATED METHODS

(71) Applicant: Rehabilitation Institute of Chicago, Chicago, IL (US)

(72) Inventors: Elliott J. Rouse, Chicago, IL (US); Christopher Nesler, Chciago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 268 days.

(21) Appl. No.: 15/347,542

(22) Filed: Nov. 9, 2016

(65) Prior Publication Data

US 2017/0128237 A1    May 11, 2017

Related U.S. Application Data

(60) Provisional application No. 62/252,914, filed on Nov. 9, 2015.

(51) Int. Cl.
| | |
|---|---|
| *F01B 19/04* | (2006.01) |
| *A61F 5/01* | (2006.01) |
| *F15B 15/10* | (2006.01) |
| *A61F 2/68* | (2006.01) |
| *A61F 2/74* | (2006.01) |
| *A61F 2/66* | (2006.01) |
| *A61H 1/02* | (2006.01) |

(52) U.S. Cl.
CPC ............ *A61F 5/0127* (2013.01); *A61F 5/012* (2013.01); *F15B 15/10* (2013.01); *A61F 2/6607* (2013.01); *A61F 2/68* (2013.01); *A61F 2002/74* (2013.01); *A61F 2002/741* (2013.01); *A61F 2005/0155* (2013.01); *A61H 1/0266* (2013.01); *A61H 2201/0103* (2013.01); *A61H 2201/1238* (2013.01); *A61H 2201/164* (2013.01); *A61H 2201/165* (2013.01); *A61H 2201/50* (2013.01)

(58) Field of Classification Search
CPC .............................. F15B 15/10; F15B 15/103
USPC ............................................................ 92/92
See application file for complete search history.

(56) References Cited

U.S. PATENT DOCUMENTS

| | | | | |
|---|---|---|---|---|
| 4,928,926 A | * | 5/1990 | Bloemendal | B66F 3/35 254/93 R |
| 5,040,452 A | * | 8/1991 | Van Kerkvoort | F15B 15/10 92/92 |
| 5,322,468 A | * | 6/1994 | Smrt | A63H 30/06 92/92 |

(Continued)

*Primary Examiner* — Michael Leslie
(74) *Attorney, Agent, or Firm* — McAndrews, Held & Malloy, Ltd.

(57) ABSTRACT

Systems and methods for providing torque to an assistive device are disclosed. In an embodiment, an apparatus comprises a material arranged to define a volume of space. The material may comprise a flexible portion and having a first surface and a second surface. The material may have a first position, in which the material is bent along the flexible portion and the first surface contacts the second surface. When the material is in the first position, an increase in pressure to the space creates a force between the first surface and the second surface. The material transitions from the first position to a second position in response to the force between the first surface and the second surface. The apparatus may be attached to an assistive device or other machine, such as an orthosis or prosthesis, in order to provide a torque.

18 Claims, 4 Drawing Sheets

(56) References Cited

U.S. PATENT DOCUMENTS

| | | | | |
|---|---|---|---|---|
| 6,901,840 B1 * | 6/2005 | Yatsko | ............... | F15B 15/103 92/89 |
| 7,100,491 B2 * | 9/2006 | Yatsko | ............... | F15B 15/103 92/92 |
| 2017/0056209 A1 * | 3/2017 | Mooney | ............. | A61F 2/6607 |

* cited by examiner

TORQUE GENERATING POUCH AND RELATED METHODS

RELATED APPLICATIONS

This patent claims priority to U.S. Provisional Patent Application Ser. No. 62/252,914, filed on Nov. 9, 2015, entitled "Torque Generating Pouch And Related Methods." The entirety of U.S. Provisional Patent Application Ser. No. 62/252,914 is incorporated herein by reference.

BACKGROUND

Assistive devices, such as prostheses, orthoses, and exoskeletons, are used in the field of physical medicine and rehabilitation. People who have lost part of their limbs, or the use of part of their limbs, rely on assistive devices for increased mobility.

BRIEF SUMMARY

In an embodiment, an apparatus comprises a material arranged to define a volume of space, the material comprising a flexible portion and having a first surface and a second surface. The material may have a first position, in which the material is bent along the flexible portion and the first surface contacts the second surface. When the material is in the first position, an increase in pressure to the space may create a force between the first surface and the second surface. The material may transition from the first position to a second position in response to the force between the first surface and the second surface.

In an embodiment, the apparatus may be coupled to a machine, and the transition from the first position to the second position provides a torque to the machine. In various embodiments, the machine may be an assistive device such as an orthosis, a prosthesis, or a joint of a prosthesis.

In an embodiment, the volume of space defined by the material may be configured to increase in pressure through receipt of a fluid. The fluid may be compressed air. In an embodiment, the space may be configured to reduce in pressure through removal of a fluid.

DETAILED DESCRIPTION

Figure 1:
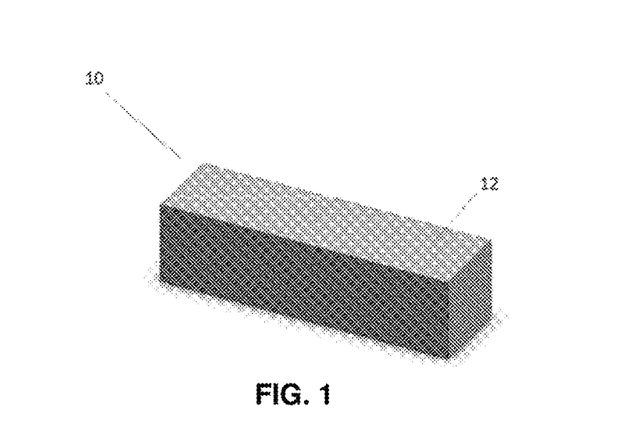
FIG. 1 is a perspective view of an embodiment of a pouch for providing torque to a machine.
Figure 2:
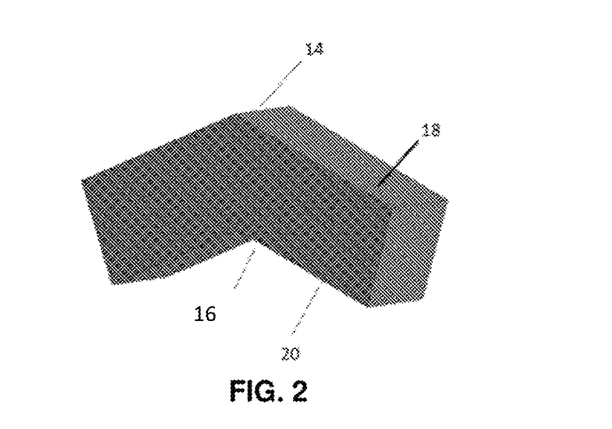
FIG. 2 is a perspective view of an embodiment of a pouch that has been bent for providing torque to a machine.
Figure 3:
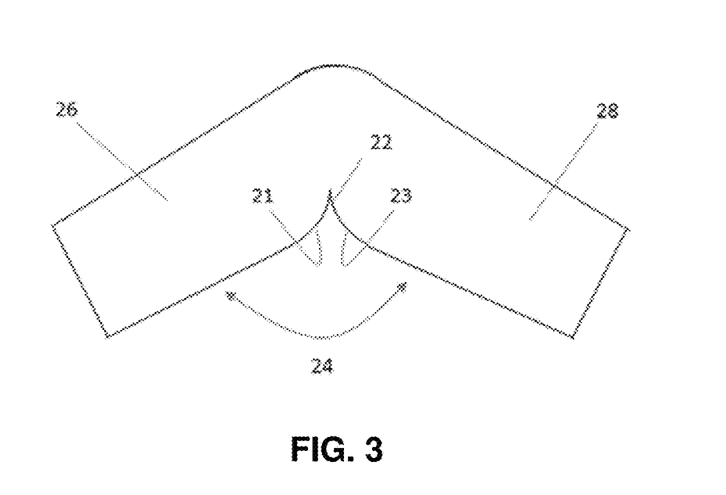
FIG. 3 is a side view of an embodiment of a pouch that has been bent for providing torque to a machine.

In one embodiment, a pouch 10 may be filled with a fluid to provide torque in a system comprising an assistive device, such as a prosthesis, orthosis, or exoskeleton. The pouch 10 may have an outer surface 12. At least a portion of the outer surface 12 may be made of a flexible material. Examples of such material may include Mylar, Kevlar, or other inelastic flexible materials. The material used to make the outer surface 12 may be a durable material. The outer surface 12 may be made of a flexible material that bends along an interface. The outer surface 12 may have a box shape, as shown in FIG. 1, or another appropriate shape. The outer surface may comprise one or more faces. The pouch 10 may be adapted to be bent at one or more positions on the outside surface 12. A bent pouch example in the shape of a box is shown in FIG. 2. For instance, when the pouch 10 has a box shape, it may be adapted to be bent at position 14 along face 18 and position 16 along face 20, as shown in FIG. 2, where position 14 is centered in face 18 and position 16 is centered in face 20. When the pouch 10 bends, a first surface 21 contacts a second surface 23 of the face 20. Where the first surface 21 contacts the second surface 23 is known as the interface. Interface 22 is shown in FIG. 3. FIG. 3 also indicates the bending angle 24, the angle made by the first surface 21 and the second surface 23. As the pouch 10 bends, the pouch 10 defines a first portion 26 on one side of the interface 22 and a second portion 28 on the other side of the interface 22. The pouch 10 may have a fixed surface area and volume that depends on the bending angle 24. Since the surface area of the pouch 10 is fixed, when the volume of the pouch 10 decreases, the pressure inside the pouch 10 increases.

Figures 4, 5:
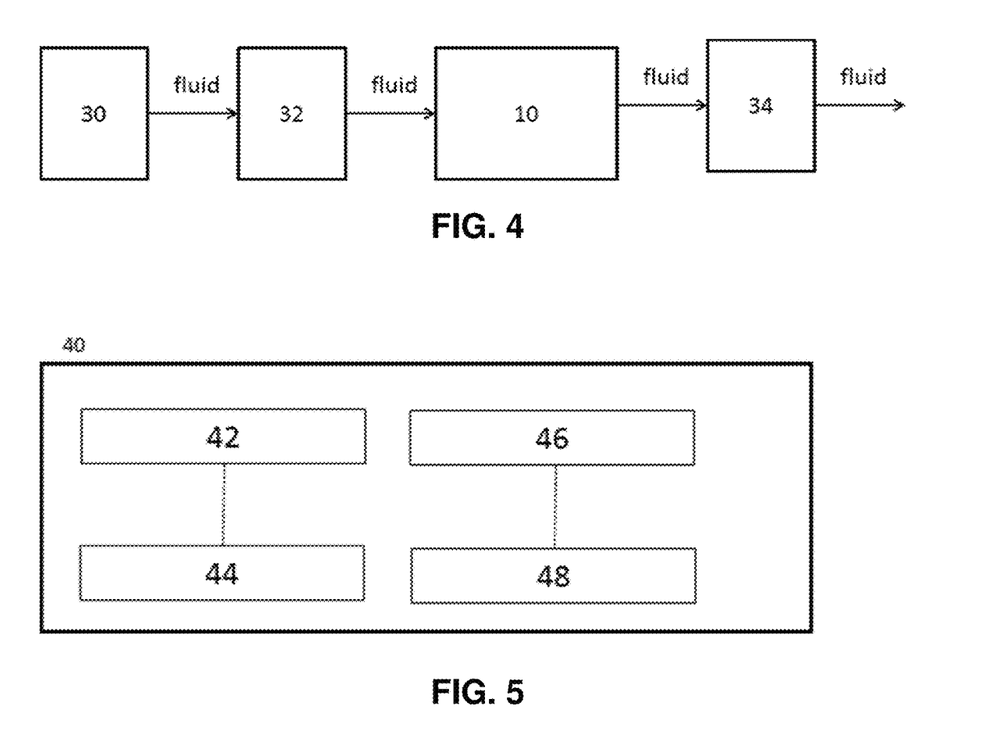
FIG. 4 is a diagram of an embodiment of a system comprising a pouch.
FIG. 5 is a diagram of an embodiment of an input valve.

The pouch 10 may be pressurized in order to provide torque to a joint of the assistive device. In an embodiment, the pouch 10 may be coupled to a fluid source 30. The fluid source 30 may provide a supply of fluid, such as compressed air. Examples include a cartridge or tank pressurizer. There are many commercially available compressed air source options, such as the Empite 40647 Basic HPA Paintball Tank Aluminum Reg—Dot, Tc 800 Psi, manufactured by Empire Brands Inc. Fluid source 30 may also provide a liquid fluid for pressurization of the pouch 10. The fluid source may be connected to the pouch 10 by an input valve 32, as shown in FIG. 4. The input valve 32 may be a solenoid valve, servo-valve, or other valve known in the art. One such valve is the Matrix 821NC 2/2 solenoid pneumatic valve, manufactured by BIBUS AG. If the input valve 32 is a solenoid valve, the input valve 32 may be controlled by passing an electric current through a solenoid. One embodiment of a solenoid valve 40 is shown in FIG. 5. The current may come from a PWM solenoid/valve driver 42, such as the DRV101 by Texas Instruments, powered by a suitable voltage supply 44. In one embodiment, the solenoid valve 40 can use a spring 46 to position an obstruction 48 in place between the interior region of the pouch 10 and the exterior of the pouch 10 when no current is applied to the solenoid valve 40. Application of current to the solenoid valve 40 causes the obstruction 48 to recede due to magnetic force, and allows the fluid from the fluid source 30 to flow down its concentration gradient into the pouch 10.

The pouch may be coupled to a joint 52 of an assistive device 50. As the joint 52 bends, it may cause the pouch 10 to bend. As the pouch 10 is bent, the volume of the pouch 10 is reduced, causing the overall pressure in the pouch 10 to increase. The additional pressure due to the bending of the pouch 10 is applied at the interface 22, as molecules within the pouch 10 try to move between the first portion 26 and the second portion 28. The pressure at the interface 22 creates a torque between the first portion 26 and the second portion 28. As fluid moves into a pouch 10 that is bent, the pressure in the pouch 10 increases, creating a torque that causes the first portion 26 and the second portion 28 to push away from each other at the interface 22. When the bending angle changes, the overlap geometry of the pouch 10 changes, which governs the way volume and angle are related.

In one embodiment, the pouch 10 may be coupled to an assistive device 50 to assist with movement of at least a portion of the assistive device 50. For example, the pouch 10 may be coupled to a joint 52 of the assistive device 50 to assist with movement of the joint 52. The pouch 10 may be positioned so that an increase in pressure in the pouch 10 causes the pouch 10 to exert a torque on the joint 52.

The torque provided by the pouch 10 may be determined as a function of other information in connection with the pouch or the assistive device. For example, the provided torque may be determined on the basis of the pressure inside the pouch 10, the shape of the pouch 10, and the bending angle of the pouch. The bending angle of the pouch 10 may be determined by a variety of sensors coupled to the pouch or the assistive device. For example, an angle encoder system may be used. Examples of angle encoder systems may include an optical disk encoder, which uses optical techniques to sense marks and/or cutouts on the pouch 10 or other appropriate locations; a magnetic encoder, which senses the bending angle through relative changes in a magnetic field as one or more appropriately placed magnets rotate; a potentiometer, which senses the bending angle through varying the drop in resistance across an appropriately placed resistor, or a fiber optic encoder, which senses the bending angle through light lost over a bending radius of an appropriately placed fiber optic cable.

One or more microcontrollers may be used in connection with the use of the pouch 10 and the assistive device 50, in order to coordinate the torque provided by the pouch 10 with the gait cycle of the user of the assistive device 50. One example is when the joint 52 comprises an artificial ankle. During the toe-off phase of gait, a human ankle provides a relatively high amount of torque to the leg for a short period of time, which propels the human body forward during walking. An artificial ankle comprising the pouch 10 may employ one or more microcontrollers (here referred to individually and collectively as microcontroller 70) to assist in the needed coordination. Additionally, the first portion 26 may be attached to a proximal portion of the artificial ankle and the second portion 28 may be attached to a distal portion of the artificial ankle. For example, as the artificial ankle enters the toe-off phase of gait, the microcontroller 70 can reduces the internal pressure P of the pouch 10 and the movement of the artificial ankle causes the pouch 10 to bend along the interface 22. When the artificial ankle is in the toe-off phase of gait, and begins to require additional torque, the microcontroller 70 can send a signal to the input valve 32, to cause the input valve 32 to open. When the input valve 32 opens, fluid from fluid source 30 is transferred into the pouch 10, increasing the pressure in the pouch 10 and causing the first surface 21 and the second surface 23 to push against each other. This creates a force along the interface 22, which causes the pouch 10 to unbend, thus providing a torque to the artificial ankle.

In one embodiment, the microcontroller 70 can determine the torque to be provided by the pouch 10 as a function of other information in connection with the pouch or the assistive device. For example, the provided torque may be determined on the basis of the pressure inside the pouch 10, the shape of the pouch 10, and the bending angle of the pouch.

In an embodiment, the microcontroller 70 determines the amount of torque ($\tau$) to be produced by the pouch 10, and then uses ($\tau$), the bending angle ($\theta$), the pouch radius (r), and the specific heat ratio ($\gamma$) to determine the internal pressure (P) inside the pouch 10. The microcontroller 70 may execute code that implements the following equation to determine the internal pressure (P) needed inside of the pouch 10 in order for the pouch 10 to provide the needed torque ($\tau$):

$$\tau(P_1, r, L, \theta) = P_1\left(\left(\frac{L}{L-2r\tan\theta}\right)^\gamma - 1\right)(-2\pi r^3(\tan^2\theta + 1)).$$

This equation is derived as follows. First, $\alpha=2*r*\tan(\theta)$, relates the length ($\alpha$) of the interface 22 to the pouch radius (r) and bending angle 24 ($\theta$). Second, the volume of the pouch 10, bent or unbent, is defined as $V=(L-\alpha)*\pi r^2$. Third, Work=$-\int P dV$, defines the work (as a function of pressure) performed over a given volume change. The pressure-volume work must be normalized to remove contribution of unbent (but pressurized) actuator, because no work is available at this resting state: Work=$\int(P-P_1)$ dV. Fourth, Work=$\int \tau d\theta$, defines the work (as a function of torque) performed over a chosen range of bending angles. For a chosen pressure, $P_1$, at the unbent (inflated) state, the pressure at the bent (inflated) state can be obtained by making the assumption that the transition from bent to unbent is an adiabatic, reversible process. This allows for the relationship $PV^\gamma$=constant to be used to solve for the pressure before the volume increases, $P_0$, in terms of $P_1$, $V_0$, and $V_1$. Combination of this expression with the equations above results in the following version of the work expression for State '0': Work=$\int(P_0-P_1)$ dV=

$$\int \left(P_1\left(\frac{L}{L-2r\tan\theta}\right)^\gamma - P_1\right)dV.$$

A change of variable substitution allows for this function to be expressed as an integral with respect to $\theta$ instead of V. For this change of variable operation, $dV/d\theta$ must be calculated from $V(\theta)=(L-2r*\tan\theta)\pi r^2$. This derivative is $V'(\theta)=-2\pi r^3 (\tan^2\theta+1)$ and, when used for the change of variable substitution, produces the following work expression:

$$\text{Work} = \int P_1\left(\left(\frac{L}{L-2r\tan\theta}\right)^\gamma - 1\right)(-2\pi r^3(\tan^2\theta + 1))d\theta.$$

Given the equivalence to the fourth equation from above (Work=$\int \tau d\theta$), this allows a closed-form expression for torque to be generated as follows:

$$\tau(P_1, r, L, \theta) = P_1\left(\left(\frac{L}{L-2r\tan\theta}\right)^\gamma - 1\right)(-2\pi r^3(\tan^2\theta + 1)).$$

Fifth, the torque $\tau$ may be divided by the term on the right hand side of the above equation to determine the needed pressure P.

In other embodiments, the pouch 10 may bend along an interface at other positions besides its center, and the performance of pouch 10 would be governed by a different set of equations to be executed by the microcontroller 70.

When fluid is released from the pouch, the pressure of the pouch decreases, reducing the torque provided by the pouch. Air may be released through an output valve 34, as shown in FIG. 4.

As mentioned above, the pouch 10 may be incorporated into different assistive devices 50, such as prostheses, orthoses, or exoskeletons. For example, one or more pouches 10 may provide assistance at one or more joints 52 where assistance is particularly needed in one direction, such as at the ankle during the period of gait surrounding toe-off.

Figure 6:
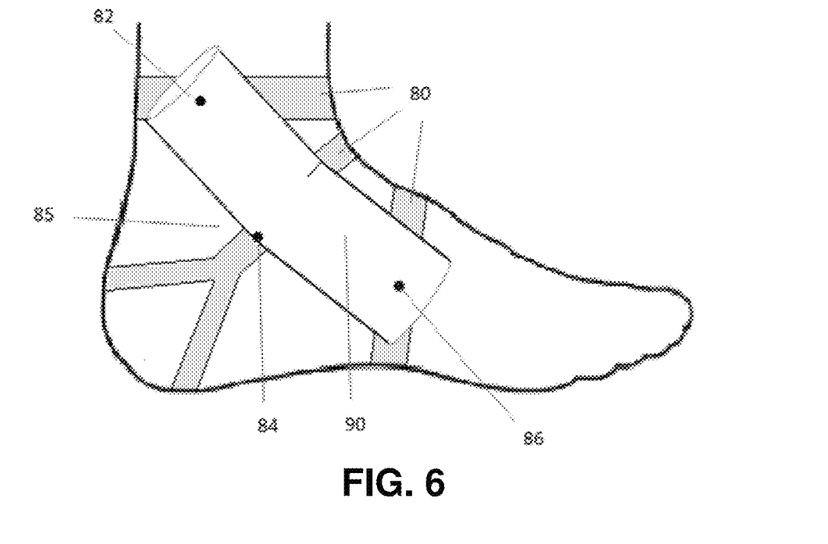
FIG. 6 is a side view of an embodiment of a pouch attached to an orthosis.

FIG. 6 displays a view of an orthosis 80 for the ankle joint 85 of a person. The orthosis 80 may be attached to a medial pouch 90, which is positioned on the inside of the ankle joint 85, and a lateral pouch 92 (not shown), which is positioned on the outside of the ankle joint 85. The medial pouch 90 may be attached to the orthosis 80 at one or more points using fasteners, such as fasteners 82, 84, and 86. The lateral pouch 92 may be similarly attached to the orthosis 80. The medial pouch 90 and the lateral pouch 92 may each be connected to a fluid source through an input valve, and may each have an output valve, as described above. The respective valves may be controlled through a microcontroller, as described above. In other embodiments, a pouch may be placed on the dorsal (i.e. top) face of the foot, for instance above the extensor retinaculum and the anterior tibila tendon. In this way a first portion of the pouch would be placed on the ventral face of the shin and a second portion of the pouch would be placed on the dorsal face of the foot.

The medial pouch 90 and the lateral pouch 92 provide torque to the ankle joint 85 during one or more phases of gait. As the foot of the ankle joint 85 starts the toe-off phase of gait, the medial pouch 90 and the lateral pouch 92 are deflated, and the plantarflexion of the foot causes the fasteners 82 and the fastener 86 to move towards one another, causing the medial pouch 90 and the lateral pouch 92 each to bend. As the medial pouch 90 and the lateral pouch 92 are bent, the volume of each pouch is reduced. At the appropriate time during the gait cycle, when the ankle needs to dorsiflex in order to complete the toe-off phase of gait and propel the person forward to the next step, the input valve to each pouch is opened, increasing the pressure in each pouch. The additional pressure is applied at the interface of each pouch, creating a torque. The torque is applied to the orthosis 80, which assists the ankle as it dorsiflexes and completes the toe-off phase of gait. After the toe-off phase is complete, the microcontroller may open the output valve of each pouch, reducing the pressure in each pouch, so that each pouch may be readied for the toe-off phase of the next step of the leg. In other embodiments, an air pouch could be used to assist a user in jumping higher.

It should be understood that the air pouch has other applications beyond being used to increase the torque available at an ankle joint of an assistive device. For instance, it may be used in the joints of astronaut suits; in hazmat or firefighter suits where additional torque would be useful to the wearer of the suit; and in other operations.

Air could be provided by various methods. For instance, a canister of compressed gas may be coupled to the air pouch. This canister could be worn on a user's back or in another appropriate location. In another embodiment, a chemical system may be employed. For instance, an electrical signal can heat a chemical such as sodium azide so that it decomposes into sodium metal and nitrogen gas, which can inflate the air pouch. In other embodiments, a vacuum system may be employed, so that the air in the air pouch is vacuumed at the appropriate moments, such as the appropriate moments in a gait cycle. One benefit of certain embodiments described in this application is that they are lightweight. For instance, the pouch 10 may be constructed of a lightweight material, which weighs far less than metal components in other assistive devices.

Figure 7:
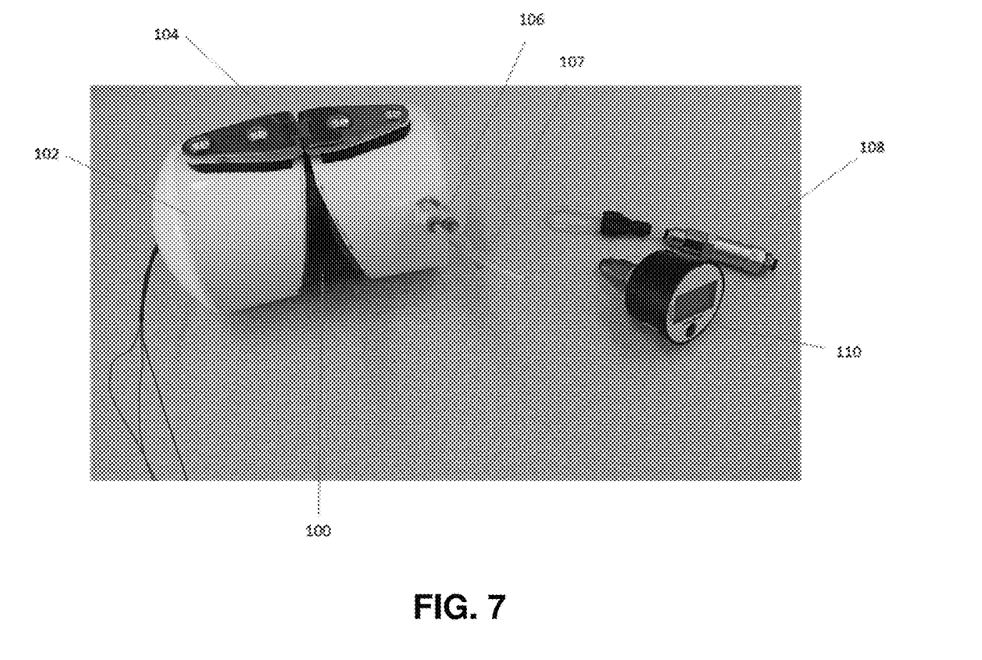
FIG. 7 is a photograph of a prototype pouch and associated components.
Figure 8:
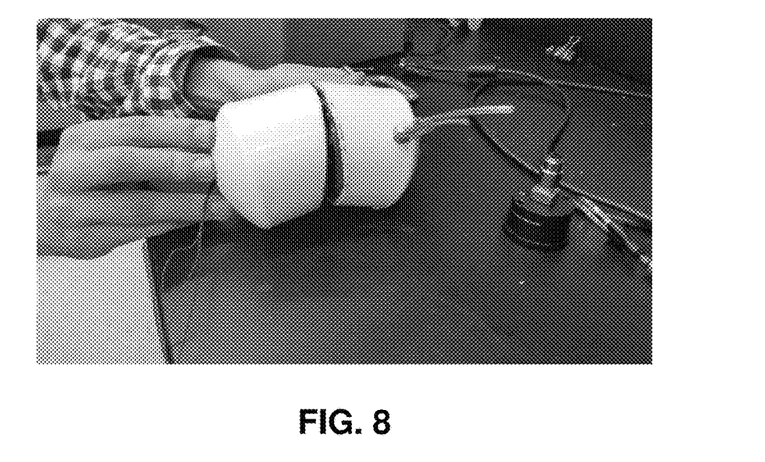
FIG. 8 is a photograph of a prototype pouch and associated components.

FIGS. 7 and 8 show photographs of a prototype pouch 100. The pouch 100 has a housing 102 made of PVC piping and ends of the housing 102 are attached by a hinge 104. The housing 102 is used to enforce the geometry of the pouch 100 for purposes of research and experimentation, and is not required in other embodiments. A source of air may be attached to the valves 106 (for instance, via flow regulator 108 and a valve tube 107). A pressure sensor 110 may be employed to test the pressure of the pouch 100. Whereas FIG. 7 shows the pouch 100 in an expanded state, FIG. 8 shows the pouch 100 compressed.

There are multiple ways to determine the appropriate time in the gait cycle to open and/or close each pouch, such as the methods disclosed in U.S. patent application Ser. No. 13/925,668, L. Hargrove and A. Young, Ambulation Prediction Controller for Assistive Device, which is incorporated by reference.

The microcontroller can operate to execute operating logic to perform one or more operations. For example, the microcontroller may include one or more computer processors that operate based on one or more sets of instructions. The sets of instructions can include one or more software applications or programs stored on a computer readable storage medium ("memory"). The memory may be a tangible and non-transitory computer readable storage medium such as a solid-state, electromagnetic, and/or optical memory. The memory can be volatile, nonvolatile, or a mixture thereof. Some or all of the memory can be portable, such as a disk, card, memory stick, cartridge, and the like. The microcontroller can include appropriate signal conditioners to transmit and receive desired information (e.g., data), and correspondingly may include filters, amplifiers, limiters, modulators, demodulators, CODECs, signal formal converters (such as analog-to-digital and digital-to-analog converters), clamps, power supplies (e.g., battery), power converters, and the like, as needed to perform various control, communication, evaluation, and processing operations described herein. The microcontroller can be comprised of one or more components of any type suitable to process input signals and provide desired output signals. Such components may include digital circuitry, analog circuitry, or a combination of both. The microcontroller can be of a programmable type; a dedicated, hard-wired state machine; or a combination of these; and can further include multiple processors, arithmetic-logic units (ALUs), central processing units (CPUs), or the like. For forms of the microcontroller with multiple processing units, distributed, pipelined, and/or parallel processing can be utilized.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second,"

and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the inventive subject matter, and also to enable any person of ordinary skill in the art to practice the embodiments disclosed herein, including making and using any devices or systems and performing any incorporated methods. The patentable scope of the subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the disclosed subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods, without departing from the spirit and scope of the subject matter herein involved, it is intended that all of the subject matter of the above description or shown in the accompanying drawings shall be interpreted merely as examples illustrating the inventive concepts herein and shall not be construed as limiting the disclosed subject matter.

What is claimed is:

1. An apparatus, comprising:
   a. a material pouch defining a volume of space, the material pouch comprising a flexible portion and having a first surface and a second surface;
   b. the material pouch having a first position, in which the material pouch is bent along the flexible portion and the first surface contacts the second surface at an interface;
   c. wherein, when the material pouch is in the first position, an increase in pressure to the space creates a force between the first surface and the second surface; and
   d. wherein the material pouch transitions from the first position to a second position in response to the force between the first surface and the second surface.

2. The apparatus of claim 1, wherein the apparatus is coupled to an assistive device and the transition from the first position to the second position resulting from increased pressure at the interface provides a torque to the assistive device.

3. The apparatus of claim 2, wherein the assistive device is an orthosis.

4. The apparatus of claim 2, wherein the assistive device is a joint of a prosthesis.

5. The apparatus of claim 1, wherein the space is configured to increase in pressure through receipt of a fluid.

6. The apparatus of claim 5, wherein the fluid is compressed air.

7. The apparatus of claim 1, wherein the space is configured to reduce in pressure through removal of a fluid.

8. The apparatus of claim 2 wherein the material pouch bends along the flexible portion when the assistive device bends.

9. A method for providing torque to a joint of an assistive device, the method comprising;
   a. providing a material pouch defining a volume of space and having a first and a second surface, the material pouch movable between a first position and a second position;
   b. positioning the material pouch adjacent the joint of the assistive device;
   c. monitoring at least one variable associated with the material pouch to determine when to provide torque to the joint of the assistive device;
   d. increasing the internal pressure in the material pouch, thereby providing torque to the joint of the assistive device.

10. The method of claim 9, wherein in the first position the material pouch is bent such that the first surface contacts the second surface at an interface.

11. The method of claim 9, wherein the material pouch further comprises an input valve, wherein the step of increasing the internal pressure comprises opening the input valve to allow pressurized fluid to enter the material pouch.

12. The method of claim 9, wherein increasing the internal pressure in the material pouch causes the first surface and the second surface to push against each other, thereby creating a force along an interface between the two surfaces, which causes the pouch to unbend.

13. The method of claim 9, further comprising reducing the internal pressure of the pouch by releasing pressurized fluid from the material pouch, thereby reducing the torque provided by the material pouch to the joint of the assistive device.

14. The method of claim 13, wherein the material pouch further comprises an output valve, wherein the step of reducing the internal pressure comprises opening the output valve to allow the pressurized fluid to leave the material pouch.

15. The method of claim 9, further comprising coordinating the torque provided by the pouch with a gait cycle of a user of the assistive device.

16. The method of claim 15, wherein the internal pressure is increased as the assistive device completes the toe-off phase of gait.

17. The method of claim 15, wherein the internal pressure is reduced as the assistive device begins the toe-off phase of gait.

18. The method of claim 9, wherein the at least one variable may comprise the internal pressure sensed inside the pouch, the shape of the pouch, or an angle between the first and the second surfaces of the pouch.

\* \* \* \* \*